(12) United States Patent
Yonekawa et al.

(10) Patent No.: US 10,389,984 B2
(45) Date of Patent: Aug. 20, 2019

(54) CRACK ANALYSIS DEVICE, CRACK ANALYSIS METHOD, AND CRACK ANALYSIS PROGRAM

(71) Applicant: Toshiba Infrastructure Systems & Solutions Corporation, Kawasaki-shi (JP)

(72) Inventors: Yoko Yonekawa, Fuchu (JP); Nobuyuki Kumakura, Sagamihara (JP); Takahiko Yamazaki, Matsudo (JP); Tomotaka Ueta, Shibuya (JP)

(73) Assignee: Toshiba Infrastructure Systems & Solutions Corporation, Kawasaki-shi (JP)

( * ) Notice: Subject to any disclaimer, the term of this patent is extended or adjusted under 35 U.S.C. 154(b) by 0 days.

(21) Appl. No.: 15/695,488

(22) Filed: Sep. 5, 2017

(65) Prior Publication Data

US 2018/0070058 A1 Mar. 8, 2018

(30) Foreign Application Priority Data

Sep. 7, 2016 (JP) ................................. 2016-174446

(51) Int. Cl.
*H04N 7/18* (2006.01)
*G08G 1/0967* (2006.01)
(Continued)

(52) U.S. Cl.
CPC ............. *H04N 7/183* (2013.01); *E01C 23/01* (2013.01); *G01N 21/88* (2013.01); *G06T 7/0004* (2013.01);
(Continued)

(58) Field of Classification Search
CPC ........ H04N 7/183; E01C 23/01; G01N 21/88; G06T 7/0002; B60G 2400/821
See application file for complete search history.

(56) References Cited

U.S. PATENT DOCUMENTS

| 6,028,948 A * | 2/2000 | Kil ........................... E01C 23/01 382/108 |
| 6,615,648 B1 * | 9/2003 | Ferguson .................. G01C 7/04 702/127 |

(Continued)

FOREIGN PATENT DOCUMENTS

| JP | 2008-15653 | 1/2008 |
| JP | 2010-176705 | 8/2010 |

(Continued)

OTHER PUBLICATIONS

Extended European Search Report dated Feb. 20, 2018 in European Patent Application No. 17189369.6, 10 pages.

(Continued)

*Primary Examiner* — Dave Czekaj
*Assistant Examiner* — Berteau Joisil
(74) *Attorney, Agent, or Firm* — Oblon, McClelland, Maier & Neustadt, L.L.P.

(57) ABSTRACT

To provide a crack analysis device, a crack analysis method, and a crack analysis program capable of correctly evaluating deterioration in a road surface.

A crack analysis device includes an image acquisition unit, a crack detector, and a display. The image acquisition unit acquires an image of a road surface. The crack detector detects cracks in which a closed region is formed on the photographed road surface based on the photographed image. The display displays a detection result of the detected cracks; and the crack detector detects the cracks which intersect each other on the road surface to form the closed region.

5 Claims, 6 Drawing Sheets

(51) Int. Cl.
*E01C 23/01* (2006.01)
*G01N 21/88* (2006.01)
*G06T 7/00* (2017.01)

(52) U.S. Cl.
CPC . *G08G 1/096716* (2013.01); *B60G 2400/821* (2013.01); *B60T 2210/14* (2013.01); *B60W 2550/14* (2013.01); *G06T 2207/30256* (2013.01)

(56) References Cited

U.S. PATENT DOCUMENTS

| | | |
|---|---|---|
| 9,129,355 B1 | 9/2015 | Harvey et al. |
| 9,390,489 B1 | 7/2016 | Harvey et al. |
| 9,805,456 B1 | 10/2017 | Harvey et al. |
| 2013/0033603 A1 | 2/2013 | Suzuki et al. |
| 2013/0173208 A1 | 7/2013 | Kuzunishi et al. |

FOREIGN PATENT DOCUMENTS

| | | |
|---|---|---|
| JP | 2012-184624 | 9/2012 |
| WO | WO 2011/108052 A1 | 9/2011 |
| WO | WO 2017/014288 A1 | 1/2017 |

OTHER PUBLICATIONS

"Method for Measuring Roughness of Pavement Surface", Japan Road Association Pavement survey and test manual, Jun. 2007, pp. 45 (with English Translation).

\* cited by examiner

CRACK ANALYSIS DEVICE, CRACK ANALYSIS METHOD, AND CRACK ANALYSIS PROGRAM

BACKGROUND OF THE INVENTION

Field of the Invention

The present invention relates to a crack analysis device, a crack analysis method, and a crack analysis program.

Description of Related Art

As a main evaluation index in measurement of road surface properties and states of asphalt paved roads, a crack percentage of pavement is used. A crack percentage is calculated in accordance with a predetermined method ("Pavement Surveying and Testing Handbook (Japan Road Association)").

However, pavement deteriorates in such a manner that cracks with line shapes increase and are spread, the pavement is eventually peeled off, and potholes (holes) progress. Past crack percentages were set as crack percentages by the number of cracks within a predetermined area. Thus, when there are two or more cracks within the predetermined area, the crack percentages were uniformly calculated as 100%. Therefore, whether cracks were spread might not be determined in some cases.

Examples of the patent literature of the related art include PCT International Publication No. WO2011/108052, Japanese Unexamined Patent Application, First Publication No. 2012-184624, Japanese Unexamined Patent Application, First Publication No. 2008-015653, and Japanese Unexamined Patent Application, First Publication No. 2010-176705.

SUMMARY OF THE INVENTION

An object of the invention is to provide a crack analysis device, a crack analysis method, and a crack analysis program capable of correctly evaluating deterioration in a road surface.

According to an embodiment, a crack analysis device includes an image acquisition unit, a crack detector, and a display. The image acquisition unit acquires an image of a road surface. The crack detector detects cracks in which a closed region is formed on the photographed road surface based on the photographed image. The display displays a detection result of the detected cracks; and the crack detector detects the cracks which intersect each other on the road surface to form the closed region.

DETAILED DESCRIPTION OF THE INVENTION

Hereinafter, a crack analysis device, a crack analysis method, and a crack analysis program according to an embodiment will be described with reference to the drawings.

In the embodiment, to correctly evaluate deterioration in a road surface, not only the number of cracks (pavement cracks) on a road surface but also a shape of the cracks will be focused on. In particular, cracks will be focused as the shape of the cracks.

Here, a crack will be described. The crack is an example of a crack in which a closed region is formed on a road surface. When deterioration in a road surface progresses, cracks occurring on a road surface become gradually longer or are branched, and thus multiple cracks intersect each other. When the multiple cracks intersect each other, the cracks form closed regions. The closed regions are, for example, polygonal or circular regions surrounded by cracks and are assumed to contain substantially closed regions of which parts are not closed. Asphalt cracks form closed regions with polygonal shapes in many cases. The shape of the asphalt crack is similar to the shell of a turtle, and thus is called a crack in some cases. In the embodiment, cracks forming closed regions are referred to as cracks in the following description. The shape of a crack is not limited to a hexagon, but is assumed to include the shape of a crack that forms a circle, an ellipse, a polygon, crocodile cracking, alligator cracking or a substantially closed region.

When cracks are finely deepened, asphalt is easily peeled due to, for example, an impact of passing vehicles. When asphalt is peeled, road surface potholes (holes) occur. The cracks are formed, in many cases, by the growth of a plurality of cracks. The cracks are assumed to include a crack with a shape in which a part of asphalt is peeled as deterioration progresses and a road surface pothole occurs.

Figure 1:
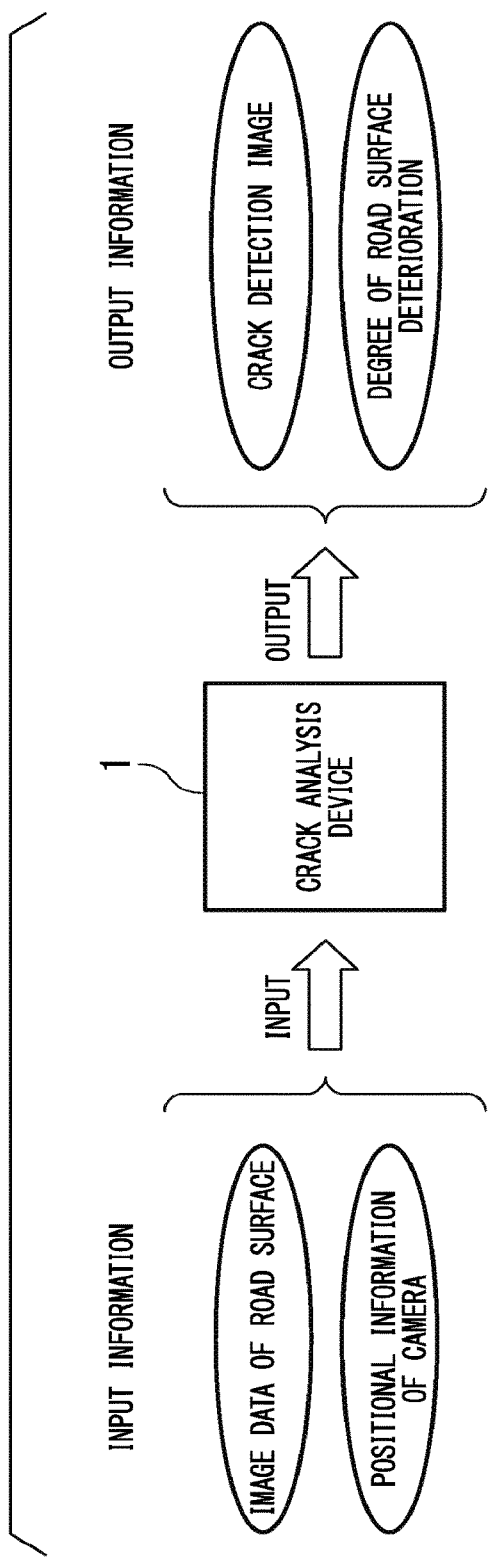
FIG. 1 is a diagram illustrating a functional overview of a crack analysis device according to an embodiment.

FIG. 1 is a diagram illustrating a functional overview of a crack analysis device according to an embodiment.

In FIG. 1, image data of a road surface and positional information of a camera are input as input information to a crack analysis device 1. The image data of the road surface is an image obtained by photographing a paved road surface with the camera. The positional information of the camera is positional information of the camera with which a paved road surface is photographed.

The crack analysis device 1 outputs a crack detection image and the degree of road surface deterioration as output information. The crack analysis device 1 detects a crack based on the input image data of the road surface and outputs a detection image for the detected crack. The crack analysis device 1 calculates and outputs the degree of road surface deterioration based on a detection result of the detected crack.

Figure 2:
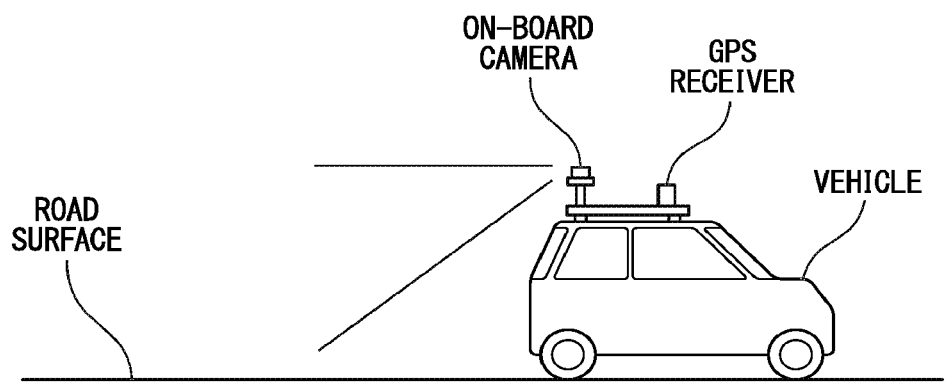
FIG. 2 is a diagram illustrating an example of a road surface photographing method according to the embodiment.

Next, a method of acquiring the image data of the road surface and the positional information of the camera input to the crack analysis device 1 will be described. FIG. 2 is a diagram illustrating an example of a road surface photographing method according to the embodiment.

In FIG. 2, an on-board camera and a Global Positioning System (GPS) receiver are mounted on the roof of a vehicle. The on-board camera photographs a road surface on the rear side of the traveling vehicle to acquire image data of the road surface. The GPS receiver acquires positional information (longitude, latitude, and altitude) of the on-board camera, a movement vehicle speed of the vehicle, a photographing time, and the like.

Figure 3:
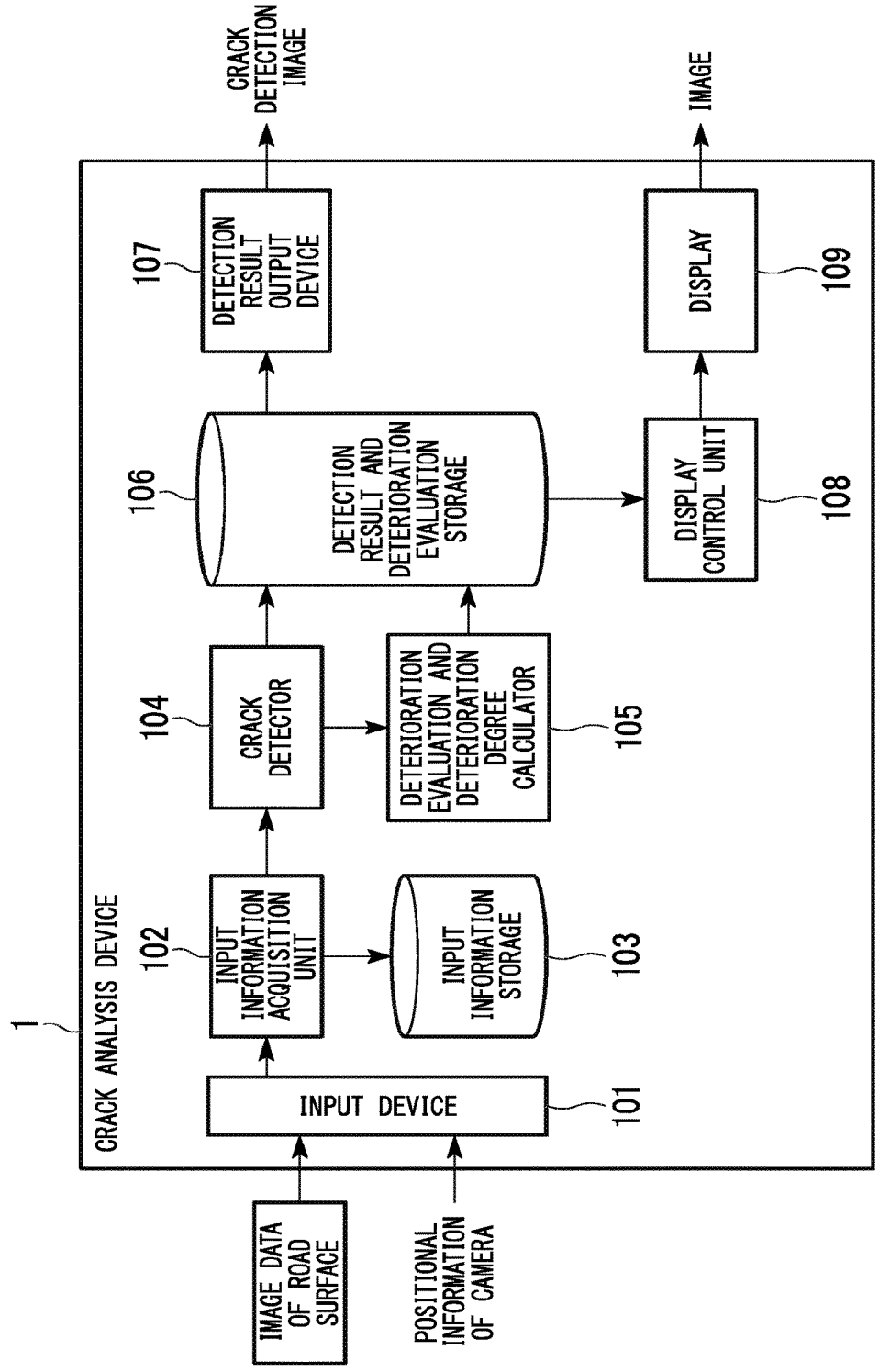
FIG. 3 is a block diagram illustrating an example of a function of the crack analysis device according to the embodiment.

Next, a function of the crack analysis device 1 will be described. FIG. 3 is a block diagram illustrating an example of the function of the crack analysis device according to the embodiment.

The crack analysis device 1 includes an input device 101, an input information acquisition unit 102, an input information storage 103, a crack detector 104, a deterioration evaluation and deterioration degree calculator 105, a detection result and deterioration evaluation storage 106, a detection result output device 107, a display control unit 108, and a display 109.

The input device 101 is, for example, a wired communication or wireless communication input interface to which the image data of the road surface photographed by the on-board camera and the positional information of the camera acquired by the GPS receiver are input.

The input information acquisition unit 102 acquires the image data of the road surface and the positional information of the camera via the input device 101 and stores the image data of the road surface and the positional information of the camera in the input information storage 103. The input information acquisition unit 102 outputs the acquired image data of the road surface and the acquired positional information of the camera to the crack detector 104.

The crack detector 104 detects a crack from the acquired image data of the road surface. The crack detector 104 records a detection result of the detected crack in the detection result and deterioration evaluation storage 106. The crack detector 104 outputs the detection result of the detected crack to the deterioration evaluation and deterioration degree calculator 105.

The deterioration evaluation and deterioration degree calculator 105 evaluates deterioration in pavement and the degree of deterioration based on the detection result of the crack acquired from the crack detector 104 and calculates the degree of deterioration. The evaluation of the deterioration and the calculation of the degree of deterioration will be described below. The deterioration evaluation and deterioration degree calculator 105 stores the evaluation of the deterioration and the calculation result of the degree of deterioration in the detection result and deterioration evaluation storage 106.

The detection result output device 107 outputs the detection result of the crack stored in the detection result and deterioration evaluation storage 106, the evaluation result evaluated by the deterioration evaluation and deterioration degree calculator 105, or information regarding the calculated degree of deterioration. The detection result output device 107 may output such information as text data, image data, print data, or the like.

The display control unit 108 generates display data for displaying the detection result of the crack stored in the detection result and deterioration evaluation storage 106, the evaluation result evaluated by the deterioration evaluation and deterioration degree calculator 105, or the information regarding the calculated degree of deterioration on the display 109 and outputs the display data to the display 109.

The display 109 performs screen display based on the display data acquired from the display control unit 108. The display 109 is, for example, a liquid crystal display.

Figure 4:
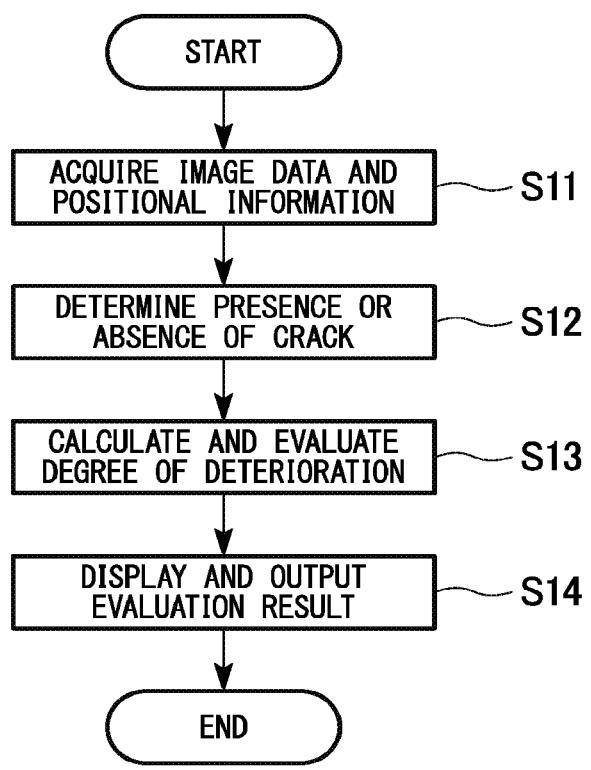
FIG. 4 is a flowchart illustrating an example of an operation of the crack analysis device according to the embodiment.

Next, an operation of the crack analysis device 1 will be described. FIG. 4 is a flowchart illustrating an example of an operation of the crack analysis device according to the embodiment.

Figure 6:
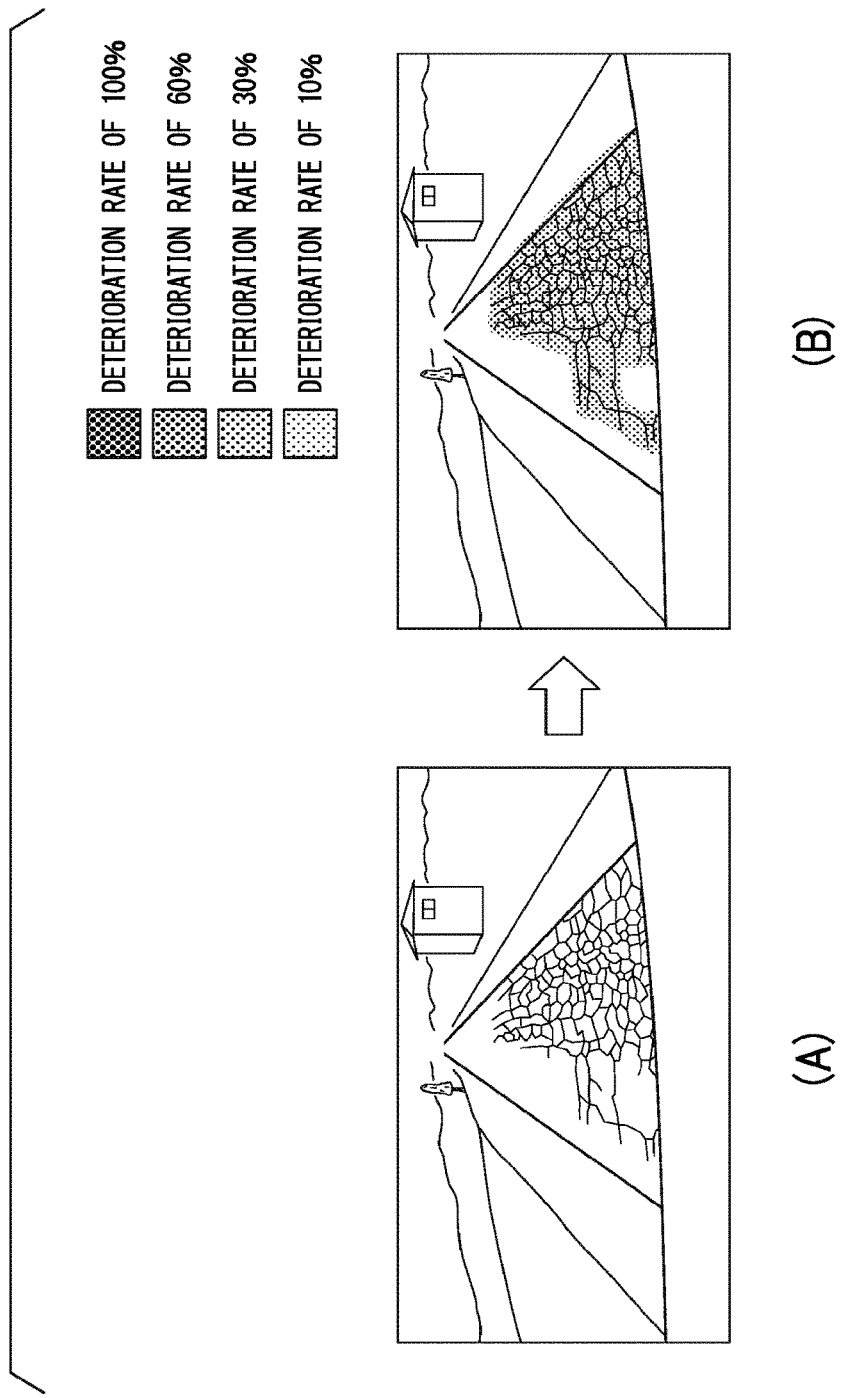
FIG. 6 is a diagram illustrating an example of an analysis result of the crack analysis device according to the embodiment.

In FIG. 4, the input information acquisition unit 102 of the crack analysis device 1 acquires the image data photographed by the on-board camera. (A) of FIG. 6 illustrates a photographed image that is photographed by the on-board camera. The input information acquisition unit 102 acquires the photographed image data and the positional information acquired by the GPS receiver and stores the image data and the positional information in the input information storage 103 (step S11). The input information acquisition unit 102 may directly acquire image data from the on-board camera connected to the input device or may acquire the image data stored in an external storage device (not illustrated). The input information acquisition unit 102 may add positional information as additional information of the acquired image data and store the additional information in the input information storage 103.

After the process of step S11 is performed, the crack analysis device 1 determines presence or absence a crack based on the acquired image data (step S12). For example, the crack detector 104 divides the acquired image data of the road surface into predetermined blocks, performs pattern matching on the image data of the divided blocks with a pre-generated crack encyclopedia, and determines whether there are cracks in the blocks. Any scheme for the pattern matching can be used.

After the process of step S12 is performed, the crack analysis device 1 calculates the degree of deterioration in the road surface and evaluates the deterioration (step S13). The details of the evaluation of the deterioration in the road surface will be described below.

After the process of step S13 is performed, the crack analysis device 1 displays the evaluation result obtained by performing the process of step S13 on the display 109 or outputs the evaluation result from the detection result output device 107 (step S14).

Next, a detailed method of evaluating the deterioration in the road surface in the process of step s13 of FIG. 4 will be described.

<Evaluation Based on Distribution of Cracks in Crossing Direction of Road>

Figure 5:
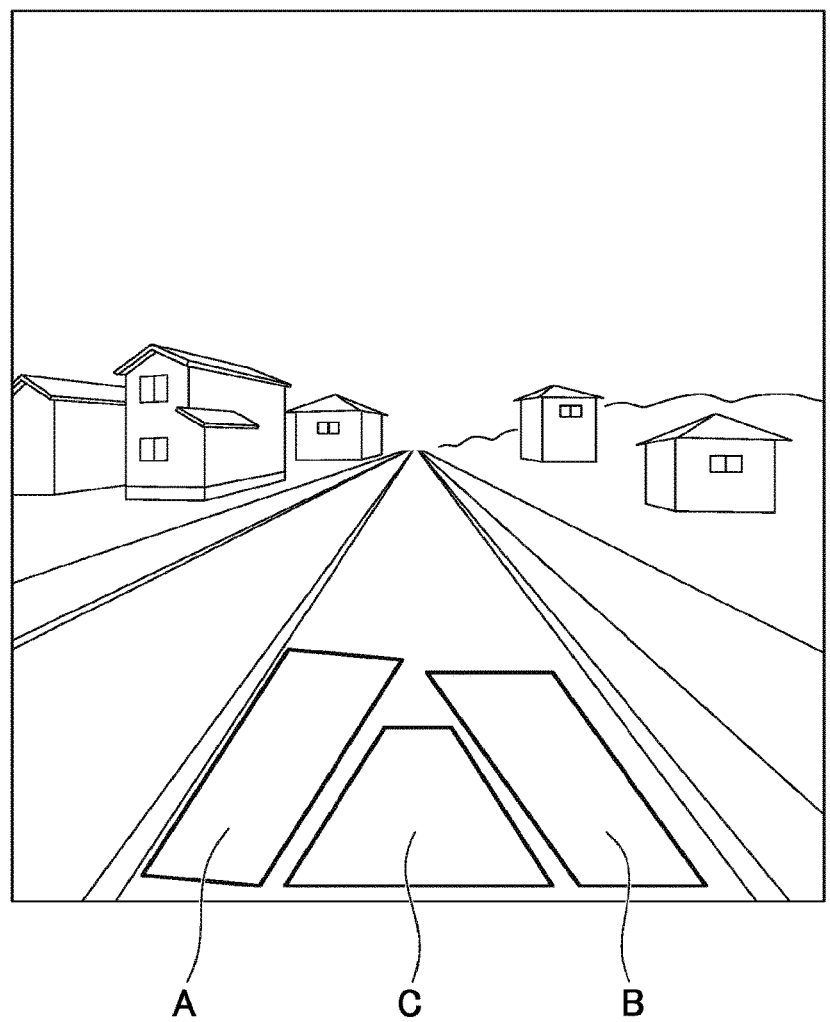
FIG. 5 is a diagram illustrating an example of a method of analyzing the crack analysis device according to the embodiment.

A method of evaluating the deterioration based on a distribution of the cracks in a crossing direction of a road will be described. FIG. 5 is a diagram illustrating an example of a method of analyzing the crack analysis device according to the embodiment.

In FIG. 5, the deterioration evaluation and deterioration degree calculator 105 determines ranges of traffic lanes in a crossing direction of a road based on the photographed image data. The ranges of the traffic lanes can be determined by recognizing an illustrated center line and side lines through image processing. The ranges of the traffic lanes may be determined, for example, by recognizing a pavement surface (asphalt) and other surfaces. The deterioration evaluation and deterioration degree calculator 105 divides the determined traffic lanes into a range (range A) of illustrated A in which right wheels of a traveling vehicle are considered to pass at a high frequency, a range (range B) of illustrated B in which left wheels of the vehicle are considered to pass at a high frequency, and a range (range C) of illustrated C in which the wheels of the traveling vehicle are considered to pass at a low frequency. The ranges A and B are ranges in which ruts easily occur. The deterioration evaluation and deterioration degree calculator 105 counts the number of occurring cracks in the divided ranges A, B, and C based on the detection result of the cracks acquired from the crack detector 104. The number of occurring cracks is, for example, the number of cracks within a predetermined distance (for example, a few cm) in the traveling direction of the road. Here, the deterioration evaluation and deterioration degree calculator 105 performs the following evaluation.

There is no crack in all of the three ranges: the degree of deterioration=10%.

There are the cracks in one of the ranges A and B: degree of deterioration=30%.

There are the cracks in both of the ranges A and B: degree of deterioration=60%.

There are the cracks in all of the three ranges: degree of deterioration=100%.

The degree of deterioration is an index which is calculated from a crack state and is suggested in the embodiment. A term such as a deterioration rate or a deterioration ratio may be used.

In the evaluation of the deterioration, for example, an average value of the degree of deterioration in a predetermined section of a road can be calculated by quantifying the deterioration as the degree of deterioration. The deterioration may be evaluated as, for example, small, intermediate, and large damage levels.

<Evaluation Based on Image in which Distribution of Cracks are Superimposed on Photographed Image>

Next, evaluation of the deterioration based on an image superimposed on a photographed image by coloring a distribution of the number of detected cracks will be described. FIG. 6 is a diagram illustrating an example of an analysis result of the crack analysis device according to the embodiment.

(A) of FIG. 6 illustrates a photographed image that is photographed by the on-board camera. An evaluation result of the deterioration is superimposed on the photographed image. The position of a road easily matches the evaluation result by superimposing the evaluation result on the photographed image.

(B) of FIG. 6 illustrates an image superimposed on the photographed image by coloring the distribution of the number of detected cracks. In the distribution of the number of cracks, when a road surface is divided into predetermined ranges (for example, a range of 1 cm×cm), whether there are cracks in each range is determined, and a numerical value obtained by averaging on a plane is colored to be superimposed on the photographed image. In (B) of FIG. 6, the depth of a color represents a hatching density. On the upper side of (B) of FIG. 6, the degrees of deterioration according to the depth of each color are displayed as a legend.

By generating the image in which the evaluation of the deterioration is superimposed on the photographed image, it is possible to instantly determine which portion of a road is deteriorating. For example, the photographed image on which the evaluation of the deterioration is superimposed is played, fast-forwarded, and paused in a traveling direction and a reverse direction of a vehicle, as in reproduction of a normal video.

According to at least one of the above-described embodiments, the crack analysis device includes a photographed image acquisition unit, a crack detector, and a display, and thus can correctly evaluate the deterioration in a road surface.

The above-described crack analysis device may be realized by a computer. In this case, a program causing a function of each functional block to be realized is recorded on a computer-readable recording medium. The program recorded on the recording medium may be read by a computer system and may be executed by a central processing unit (CPU) to be realized. Here, the "computer system" is assumed to include an operating system (OS) and hardware such as a peripheral device. The "computer-readable recording medium" refers to a portable medium such as a flexible disc, a magneto-optical disc, a read-only memory (ROM), or a CD-ROM. The "computer-readable recording medium" includes a storage device such as a hard disk built-in in the computer system. Further, the "computer-readable recording medium" may include a portion that dynamically retains a program for a short time. The portion that dynamically retains the program for a short time is, for example, a communication line when the program is transmitted via a network such as the Internet or a communication line such as a telephone line. The "computer-readable recording medium" may include a portion that retains the program for a given time, such as a volatile memory inside a computer system serving as a server or a client. The program may be a program that realizes some of the above-described functions. The program may realize the above-described functions in combination with a program already recorded on the computer system. The program may be a program realized using a programmable logic device. The programmable logic device is, for example, a field programmable gate array (FPGA).

Although each functional unit of the foregoing device has been described as a software functional unit, some or all of the functions of the crack analysis device 1 may be hardware functional units such as LSI.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A crack analysis device comprising
an image acquisition unit configured to acquire an image of a road surface;
a crack detector configured to detect cracks in which a closed region is formed on the photographed road surface based on the photographed image; and
a display configured to display a detection result of the detected cracks; and
a deterioration degree calculator configured to calculate a degree of deterioration of the road surface in accordance with a range of the road surface on which the cracks are detected,
wherein the crack detector detects the cracks which intersect each other on the road surface to form the closed region,
the display performs display in accordance with the calculated degree of deterioration so that the display is superimposed on the photographed image, and
the deterioration degree calculator divides a range of the road surface into ranges of a wheel passage portion and other portions in a crossing direction of a road and calculates the degree of deterioration in the road surface in accordance with presence of the cracks within each of the divided ranges.

2. The crack analysis device according to claim 1,
wherein the deterioration degree calculator counts the number of detected cracks in the divided ranges; and
the deterioration degree calculator configured to make an evaluation on deterioration of the road surface based on the number of each counted cracks in the divided ranges.

3. The crack analysis device according to claim 2,
wherein the deterioration degree calculator makes an evaluation on deterioration of the road surface, based on an average calculated from a respective degree of deterioration of each of multiple adjacent areas of the road surface.

4. A crack analysis method comprising:
acquiring a photographed image obtained by photographing a road surface;
detecting cracks in which a closed region is formed on the photographed road surface based on the photographed image; and
displaying a detection result of the detected cracks;
calculating a degree of deterioration of the road surface in accordance with a range of the road surface on which the cracks are detected; and
wherein detecting detects the cracks which intersect each other on the road surface to form the closed region,
performing display in accordance with the calculated degree of deterioration so that the display is superimposed on the photographed image, and
dividing a range of the road surface into ranges of a wheel passage portion and other portions in a crossing direction of a road and calculates the degree of deterioration in the road surface in accordance with presence of the cracks within each of the divided ranges.

5. A non-transitory computer readable storage medium that stores a crack analysis program to be executed by a computer to cause the computer to perform:

a photographed image acquisition process of acquiring a photographed image obtained by photographing a road surface;
a crack detection process of detecting cracks in which a closed region is formed on the photographed road surface based on the photographed image;
a display process of displaying a detection result of the detected cracks; and
a deterioration degree calculation process of calculating a degree of deterioration of the road surface in accordance with a range of the road surface on which the cracks are detected,
wherein the crack detection process of detecting cracks which intersect each other on the road surface to form the closed region,
the display process of performing display in accordance with the calculated degree of deterioration so that the display is superimposed on the photographed image, and
the deterioration degree calculation process of dividing a range of the road surface into ranges of a wheel passage portion and other portions in a crossing direction of a road and calculates the degree of deterioration in the road surface in accordance with presence of the cracks within each of the divided ranges.

* * * * *